US011019158B2

(12) United States Patent
Protas et al.

(10) Patent No.: US 11,019,158 B2
(45) Date of Patent: *May 25, 2021

(54) REAL-TIME DATA DISTRIBUTION SYSTEM FOR PATIENT MONITORING DEVICES, CARDIAC DEFIBRILLATORS AND ASSOCIATED INFORMATION DELIVERY SYSTEMS

(71) Applicant: Physio-Control, Inc., Redmond, WA (US)

(72) Inventors: Cheryl Protas, Pleasanton, CA (US); James Wootten, Kirkland, WA (US); Seshadri Kumar Padmanabha, Redmond, WA (US); Ken Peterson, Bellevue, WA (US); Randy Merry, Woodinville, WA (US); David Stewart, Carnation, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/377,784

(22) Filed: Apr. 8, 2019

(65) Prior Publication Data

US 2019/0238643 A1 Aug. 1, 2019

Related U.S. Application Data

(63) Continuation of application No. 14/470,880, filed on Aug. 27, 2014, now Pat. No. 10,257,287.
(Continued)

(51) Int. Cl.
*H04L 29/08* (2006.01)
*G16H 40/63* (2018.01)
(Continued)

(52) U.S. Cl.
CPC ............ *H04L 67/16* (2013.01); *G16H 40/63* (2018.01); *G16H 40/67* (2018.01); *H04L 67/10* (2013.01);
(Continued)

(58) Field of Classification Search
None
See application file for complete search history.

(56) References Cited

U.S. PATENT DOCUMENTS 6,579,231 B1 6/2003 Phipps
6,697,103 B1 2/2004 Fernandez et al.
(Continued)

FOREIGN PATENT DOCUMENTS

WO 2008/098346 A1 8/2008

OTHER PUBLICATIONS

Koerner; "Your Cellphone is a Homing Device"; www.legalaffairs.org/issues/July-August-2003/feature_koerner_julaug03.msp; Jul./Aug. 2003; accessed Sep. 10, 2014; 6 pages.
(Continued)

*Primary Examiner* — James A Edwards
(74) *Attorney, Agent, or Firm* — McDonnell Boehnen Hulbert & Berghoff LLP

(57) ABSTRACT

A data distribution system in comprises software application nodes that utilize a publish-subscribe communication mechanism for distribution of data in real-time or near real-time within a personal area network (PAN), local area network (LAN), or wide-area network (WAN) configuration. The distributed system communication software application nodes reside in medical devices, such as monitoring devices and cardiac defibrillators, and associated patient information delivery systems and patient data management systems comprising medical software installed on servers and end-user computing devices, including mobile devices.

18 Claims, 2 Drawing Sheets

Related U.S. Application Data

(60) Provisional application No. 61/871,271, filed on Aug. 28, 2013.

(51) Int. Cl.
  *G16H 40/67* (2018.01)
  *G06F 15/173* (2006.01)
  *A61B 5/00* (2006.01)
  *H04L 12/46* (2006.01)
  *H04W 4/80* (2018.01)

(52) U.S. Cl.
  CPC .......... *A61B 5/0022* (2013.01); *G06F 15/173* (2013.01); *H04L 12/4604* (2013.01); *H04L 29/08* (2013.01); *H04W 4/80* (2018.02)

(56) References Cited

U.S. PATENT DOCUMENTS

| | | | |
|---|---|---|---|
| 6,790,044 | B1 | 9/2004 | Haegebarth |
| 7,349,947 | B1 | 3/2008 | Slage et al. |
| 7,614,001 | B2 | 11/2009 | Abbott et al. |
| 7,733,244 | B2 | 6/2010 | Tran |
| 8,171,094 | B2 * | 5/2012 | Chan ................... G06F 19/3418 709/206 |
| 8,185,623 | B2 | 5/2012 | Lewis et al. |
| 8,591,455 | B2 | 11/2013 | Mensinger et al. |
| 8,684,922 | B2 | 4/2014 | Tran |
| 8,750,971 | B2 | 6/2014 | Tran |
| 8,755,821 | B2 | 6/2014 | Brisebois et al. |
| 8,764,651 | B2 | 7/2014 | Tran |
| 9,079,306 | B2 | 7/2015 | Ng-Thow-Hing et al. |
| 2002/0019584 | A1 | 2/2002 | Schulze et al. |
| 2002/0129106 | A1 | 9/2002 | Gutfreund |
| 2004/0054918 | A1 | 3/2004 | Duri et al. |
| 2008/0101160 | A1 | 5/2008 | Besson |
| 2009/0054735 | A1 | 2/2009 | Higgins et al. |
| 2009/0099480 | A1 | 4/2009 | Salgo et al. |
| 2009/0105879 | A1 | 4/2009 | Ng-Thow-Hing et al. |
| 2009/0177477 | A1 | 7/2009 | Nenov et al. |
| 2010/0205205 | A1 | 8/2010 | Hamel |
| 2010/0315225 | A1 | 12/2010 | Teague |
| 2011/0125921 | A1 | 5/2011 | Karenos et al. |
| 2011/0161103 | A1 | 6/2011 | Dye et al. |
| 2012/0242501 | A1 * | 9/2012 | Tran ..................... A61B 5/0024 340/870.02 |
| 2013/0024213 | A1 | 1/2013 | Poon |
| 2013/0099918 | A1 | 4/2013 | Dunst et al. |
| 2014/0028464 | A1 * | 1/2014 | Garibaldi ............... G16H 50/70 340/870.02 |

OTHER PUBLICATIONS

Lee et al.; "Biomedical Telemedicine"; Handout; CSCI-170; Jan. 11, 2005; 16 pages.

Powers; Status of a Commercial Physiological Status Monitoring (PSM) System; QinetiQ North America; 2009; 14 pages.

Arulogun; "IPv6 Based Wireless Sensor Networks Electronic Health Monitoring System"; Proceedings of the Fourth Int'l Conf. on Mobile e-Services; vol. 4; Oct. 2012; p. 11-17.

"BioHarness 3 Team Compression Shirts"; www.zephyranywherestore.com/BioHarness-3-Team-Compression-Shirts/dp/B009ZT; Zephyr Technology Corp.; 2012; accessed Sep. 9, 2014, 2 pages.

Patel et al.; "A Review of Wearable Sensors and Systems with Applications in Rehabilitation"; Journal of Neuroengineering and Rehab; 2012; 9:21; p. 1-17.

"5 wearable technologies for EMS"; www.ems1.com/technology/articles/1861982-5-wearable-technologies-for-EMS; 2014; access Sep. 9, 2014; 3 pages.

"High Fidelity Alarm Analytics"; www.visimobile.com/visi-product-info/high-fidelity-alarm-analytics/; access Sep. 9, 2014; 2 pages.

* cited by examiner

REAL-TIME DATA DISTRIBUTION SYSTEM FOR PATIENT MONITORING DEVICES, CARDIAC DEFIBRILLATORS AND ASSOCIATED INFORMATION DELIVERY SYSTEMS

CROSS-REFERENCE TO RELATED APPLICATIONS

This application is a continuation of U.S. patent application Ser. No. 14/470,880 filed on Aug. 27, 2014, which claims the benefit of Provisional U.S. Provisional Patent Application Ser. No. 61/871,271 filed on Aug. 28, 2013, the entire contents of each of which are hereby incorporated by reference.

TECHNICAL FIELD

The present invention relates generally to medical devices including defibrillators, and more particularly to a data distribution system configured to distribute patient medical data in real-time or near real-time.

SUMMARY

A data distribution system in accordance with an illustrative embodiment comprises a personal area network (PAN) comprising a first PAN node and a second PAN node, and a PAN data blackboard, wherein the first PAN node comprises a first medical device configured for monitoring a first patient. In addition, the inventive system may include a wide area network (WAN) comprising a WAN data blackboard coupled to the PAN data blackboard, and a WAN data management node. The PAN data blackboard is configured to provide a data storage space shared among the first and second PAN nodes. In the illustrative embodiment, data blackboards are used in PAN, LAN, and WAN communications, and a separate blackboard is used for each type of communication.

In the illustrative embodiment, the first PAN node is configured as publisher node, whereby the first PAN node writes data to the PAN data blackboard, and the second PAN node is configured as a subscriber node, whereby the second PAN node reads data from the PAN data blackboard. The data distribution system of the illustrative embodiment also includes a local area network (LAN) comprising a first LAN node, a second LAN node, a LAN data blackboard, and a LAN data management node. As discussed below, a WAN data blackboard may also be used for WAN communications.

Other features of the illustrative embodiment are described below.

DETAILED DESCRIPTION OF ILLUSTRATIVE EMBODIMENTS

Data Distribution System and Method

An illustrative embodiment of a data distribution system in accordance with the present invention comprises software application nodes that utilize a publish-subscribe communication mechanism for distribution of data in real-time or near real-time within a personal area network (PAN), local area network (LAN), or wide-area network (WAN) configuration. The distributed system communication software application nodes reside in medical devices, such as monitoring devices and cardiac defibrillators, and associated patient information delivery systems and patient data management systems comprising medical software installed on servers and end-user computing devices, including mobile devices.

Figure 1:
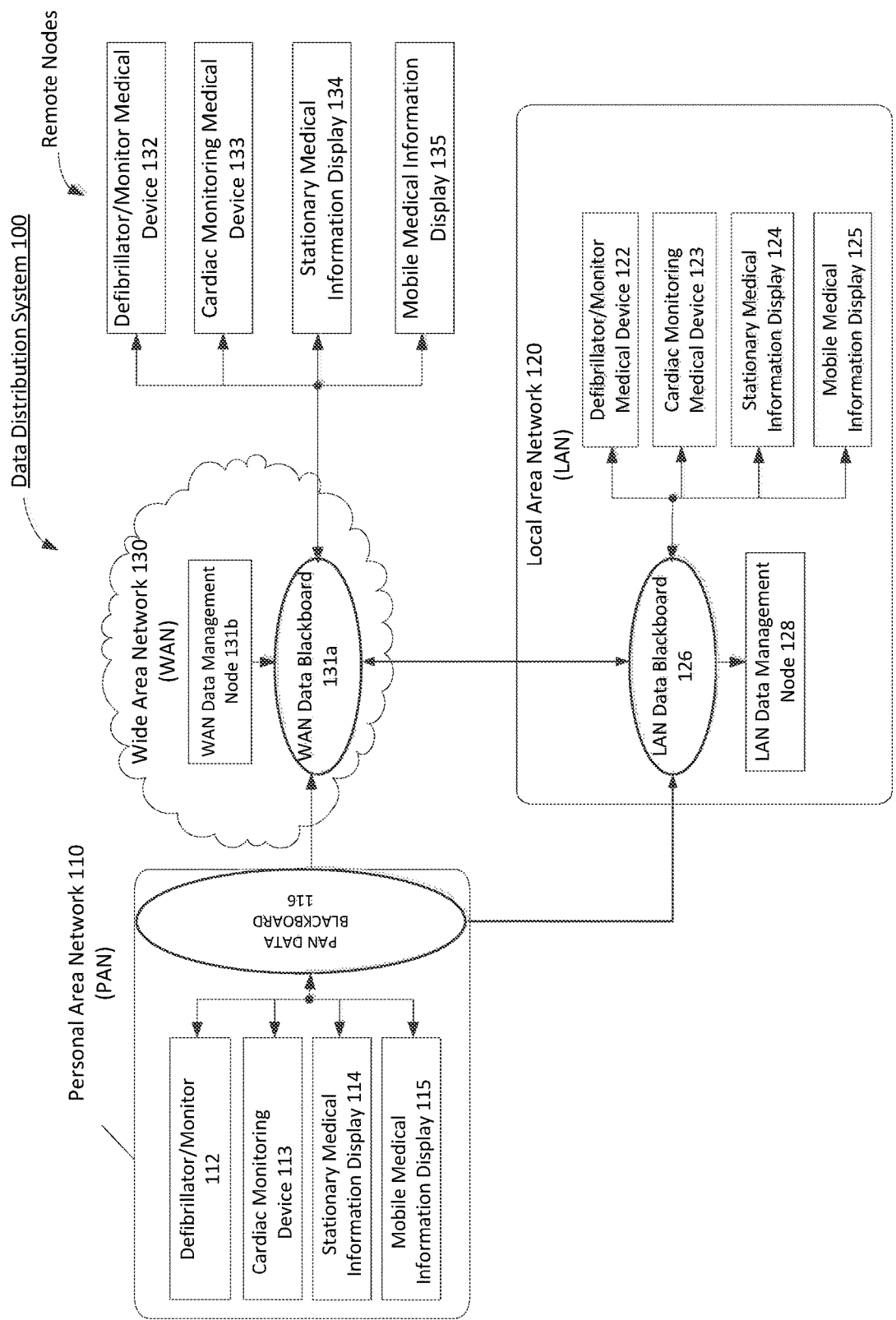
FIG. 1 is a block diagram of an illustrative embodiment of a data distribution system in accordance with the present invention.

Referring to FIG. 1, in the illustrative embodiment, the data distribution system 100 may include or employ a personal area network (PAN) 110, a local area network (LAN) 120, and/or a wide area network (WAN) 130. The PAN 110 includes various nodes, including a defibrillator/monitor 112, a cardiac monitoring device 113, a stationary medical information display 114, and a mobile medical information display 115. It will be understood by those skilled in the art that these are just exemplary medical sensing or display devices, and that a given system may include only a subset of these or all of these plus additional nodes. The nodes are operatively connected to a PAN data blackboard 116. Each of the various nodes can be configured as a "publisher" or "subscriber" of data (or both), and the PAN data blackboard and the other blackboards (i.e., 126 and 131a) provide a data space that can be shared by the connected publisher and subscriber nodes. As used herein, the term "blackboard" refers to a shared memory structure.

Similarly, the LAN 120 includes various nodes including a defibrillator/monitor medical device 122, a cardiac monitoring device 123, a stationary medical information display 124, and a mobile medical information display 125. Here again, it will be understood by those skilled in the art that these are just exemplary medical sensing or display devices, and that a given system may include only a subset of these or all of these plus additional nodes. The nodes are operatively connected to a LAN data blackboard 126, and the LAN data blackboard 126 is connected to a LAN data management node 128. The LAN data management node 128 (as well as the WAN data management node 133) is configured to mediate the communication channels, ensuring subscribers have access to published data they are entitled to access, and do not have access to published data they are not entitled to access. The data management nodes may also perform certain processor intensive activities (in other words, data analytics) and long term data storage tasks.

Finally, referring to FIG. 1, the WAN 130 includes the WAN data blackboard 131a and the WAN data management node 131b, and is operatively connected to various nodes, e.g., a defibrillator/monitor medical device 132, a cardiac monitoring device 133, a stationary medical information display 134, and a mobile medical information display 135. It should be noted that the number of subscribers/publishers, including medical device nodes, is limited by the available resource on the particular network configuration. For example, a single PAN may support approximately 5-10 devices depending on wireless capability, bandwidth, memory constraints at each node, processing constraints at each node, etc. On the other hand, a single LAN may support hundreds of devices (concurrently), and a WAN may support thousands of devices (concurrently).

The overall data distribution system 100 can:

Be localized to devices connected in an ad-hoc personal area network (PAN).

Be geographically dispersed via a wide area network (WAN), i.e., by way of wired or wireless connections of nodes over the Internet.

Be a local area network (LAN) or virtualized local area network (VLAN) of wired or wirelessly connected nodes.

Comprise various computing hardware and operating systems.

Enable all nodes to publish information to other nodes and subscribe to information from other nodes.

Ensure multiple subscriber nodes can receive medical event information that is published just once by another node.

Medical Data Monitoring and Distribution Method

Figure 2:
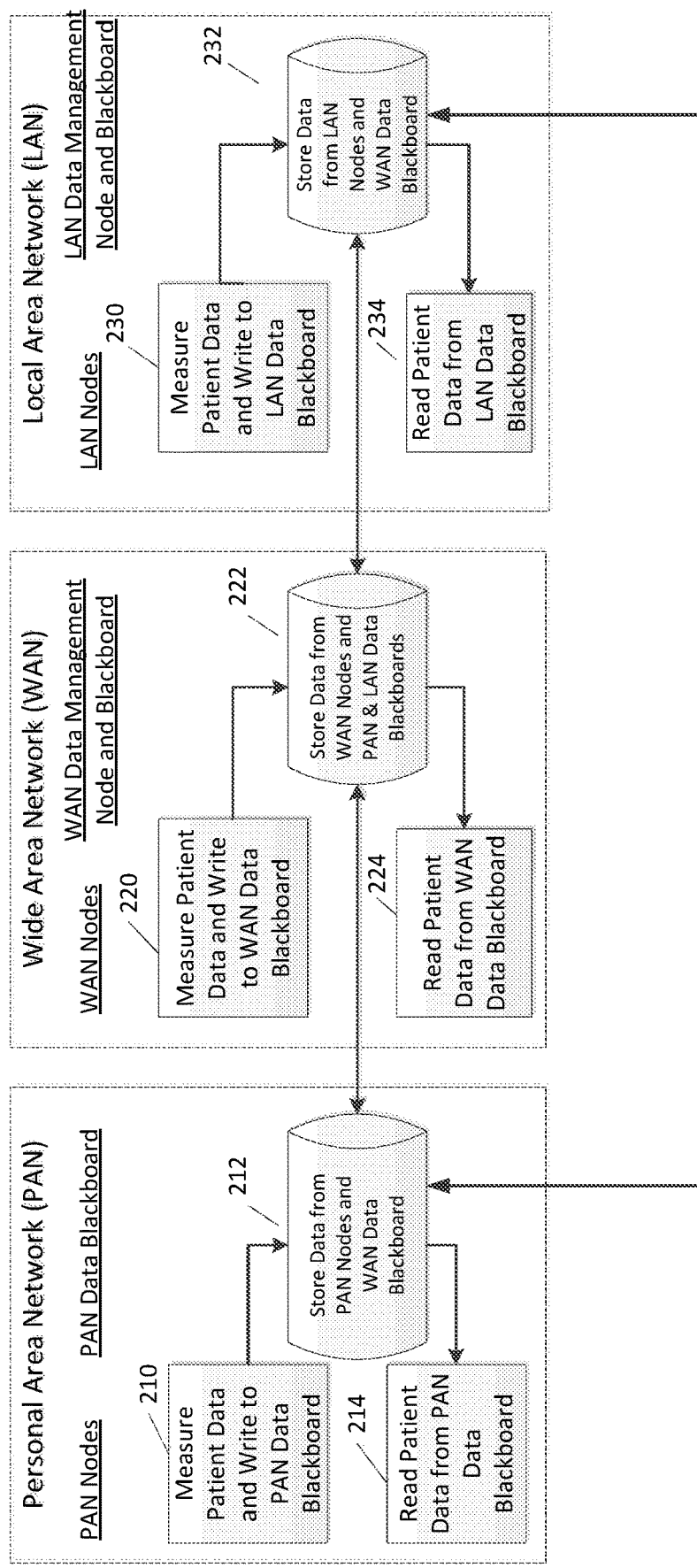
FIG. 2 is a flowchart of a medical data monitoring and distribution method in accordance with the present invention.

FIG. 2 depicts an illustrative embodiment of a medical data monitoring and distribution method in accordance with the present invention. As discussed above, the inventive system operates according to a method in which a first node of a personal area network (PAN) is used to monitor a first patient and write medical data to a PAN data blackboard. A second PAN node, which may be contained within in a second medical device, reads data from the PAN data blackboard. Moreover, as discussed, the PAN data blackboard may be coupled to a WAN data blackboard, which may in turn be coupled to a remote LAN data blackboard, and both the WAN and LAN data blackboards may be coupled to respective medical devices and nodes.

As shown in FIG. 2, in a PAN, a first PAN node measures patient data and writes this data to the PAN data blackboard (step 210). The PAN data blackboard stores the data and may also store selected data from the WAN data blackboard (step 212); and a second LAN node reads selected data from the PAN data blackboard (step 214).

Similarly, in a WAN, a first WAN node measures patient data and writes this data to the WAN data blackboard (step 220), and the WAN data blackboard stores the data and may also store selected data from the PAN and LAN data blackboards (step 222). A second WAN node may be deployed to read selected data from the WAN data blackboard (step 224).

Finally, in the LAN (far right box of FIG. 2), a first LAN node measures patient data and writes this data to the LAN data blackboard (step 230). The LAN data blackboard stores the data and may also store selected data from the WAN data blackboard (step 232); and a second LAN node reads selected data from the LAN data blackboard (step 234).

Further Details of Illustrative Uses

The inventive data distribution system and method may be used to:

Distribute medical event information between local and remote nodes in the data distribution system. Such medical event information can include data, audio and video streams, and consumable electronic object formats.

Distribute information for shared viewing of information that is continuously updated (i.e., in "real-time" or by "live streaming") on one or more subscribing nodes when changed on the publisher node. For example, an ECG lead sensor reading may be distributed every 0.25 ms, or updated on a discrete interval, or may be considered a "batch" mode operation where information is bundled periodically on a publisher node and broadcast to subscriber nodes. For example, a sync timer may be used, or an intermittent event; for example, a lead placement indicator may be used.

Distribute software and configuration updates within the data distribution system.

Distribute commands between local and remote nodes in the data distribution system. A distributed command is an instruction by one node to one or more other nodes to perform an action. An example is a command to start a timer, silence an alarm, etc.

Conduct remote diagnostics of equipment.

Distribute algorithms for processing ("analytics") across nodes of the data distribution system.

Data Blackboard (see elements 116, 126, and 131*a* in FIG. 1)—a data space shared among connected publisher and subscriber nodes to enable publication (write) and subscription (read).

Node (see elements 112-115, 122-125, and 132-135 of FIG. 1)—each node is a publisher/subscriber of a Data Blackboard. Node Types may include Information Management System, Defibrillator/Monitor, Monitoring Device, Stationary Medical Information Display, Mobile Medical Information Display.

PAN Data Distribution System: nodes dynamically form a wireless personal area network based on close proximity (e.g., patient home, military battle field, movie theater) sharing a Data Blackboard for point-to-point publish-subscribe communication within the PAN. Many PAN instances may exist concurrently.

LAN Data Distribution System: wired and wireless nodes participate in a local area network. Wireless nodes join the network via one or more network access points. LAN nodes participate in publish-subscribe communication using LAN network infrastructure. LANs are created for organizational entities such as a patient care facility (e.g., Hospital, Emergency Room), or patient care organization (e.g., Hospital Network)

WAN Data Distribution System: Servers residing in data centers enable publishers and subscribers to span a broader geographic spectrum than a PAN or LAN. The WAN servers bridge the communication between PAN and LAN nodes, as well as publish-subscribe nodes connected directly.

Each Data Blackboard selectively synchronizes data with other Data Blackboards, thereby enabling communication with nodes connected to another bus. The Data Management Nodes mediate the communication channels, ensuring subscribers have access to published data they are entitled to access, and do not have access to published data they are not entitle to access. The Data Management Nodes may also offload processor intensive activities and long term data storage requirements from other Data Distribution System nodes.

Further Illustrative Details of how it Works

Node Capability:

Each node in the distributed system has the capability to both publish (provide data) and subscribe (consume data). The communication nodes participate in the distributed system as either publishers, or subscribers, or both.

A subscriber may perform content filtering on published streams. In other words, a subscriber can be selective regarding what it receives from a publisher. In other words, a publisher may publish more than the subscriber receives.

Data Types:
  Each node publishes and\or subscribes to a data channel for exchange of discrete data, audio and video streams, and binary objects.
Data Sources:
  The data source for publication may be bio-sensors, medical information systems, externally connected medical device accessories, user entered information, and/or the results from algorithms/processor intensive activities/data summarization of a node.
Communication Channel Types:
  Distributed system nodes may communicate in the data distribution system via wired network connection or wireless network connection. Wireless network connections include Wi-Fi™, Wi-Fi Direct™ and Bluetooth® Standard, Bluetooth® PAN, and Cellular.
Communication Channel Middleware:
  The data distribution system may include messaging middleware that enables the publishers and subscribers to function autonomously (i.e., "decoupled").
Communication Protocol and Data Format Standards
  The Data Distribution System may implement a standard messaging protocol for publish-subscribe communications such as Message Queuing for Telemetry Transport (MQTT) or Advanced Message Queuing Protocol.
  The Data Distribution System may alternatively comprise shared data spaces, which also decouples publishers and subscribers. A standard protocol for distributed data communication using shared data spaces is the Object Management Group Data-Distribution Service for Real-Time Systems (DDS).
  Other standard protocols for communication are UDP and TCP/IP
  Data payload may employ data format and\or semantics as defined by the following standards: IEEE 11073, HL7, IHE Domains such as Infrastructure, PCD, and the IHE CDA\CCD, and NEMSIS XML.
Communication Attributes:
  Published data is persistent; a "late" subscriber may obtain published data for a defined interval following its publication.
  Publication is reliable; a publisher will postpone publication until a lost connection is restored or an unavailable connection becomes available.
  The publication is auto-scaled (also "auto-adjusted) based on available bandwidth, thereby reducing or increasing the amount or frequency of data, or selectively eliminating lower-priority data to give bandwidth for higher priority data.
  The publication/subscription capability on each node minimizes bandwidth requirement and battery consumption, thereby allowing interconnected mobile battery powered nodes.
  Publication may be multi-cast (many publishers, many subscribers) or unicast (one publisher, one subscriber).
Communication Isolation
  The Data Distribution System enforces constraints necessarily to ensure data privacy and to enable nodes to operate within resource limitations (memory, storage, battery, etc.); publishers are necessarily constrained by where to publish, when to publish, and what to publish. Subscribers are constrained by which publications they have access to, when they receive the publication, and how much they can receive due to limited subscriber resources (memory, storage, battery, etc.).

Communication Sustainability Across Networks
  Distributed system nodes may participate in publish-subscribe communications over several network interfaces concurrently or serially.
  The data distribution system enables a bridge for communications across network interfaces, allowing publishers and subscribers to reside on separate networks.
  Distributed system nodes including publishers and subscribers may switch network connections, allowing a subscriber to continue to receive data from a publisher after the switchover.
  Distributed system nodes may implement a priority scheme to expedite a connection switch based on connection speed, connection strength, or service discovery\accessibility.

CONCLUSION

One skilled in the art will appreciate that the present teachings can be practiced with embodiments other than those disclosed above. The disclosed embodiments are presented for purposes of illustration and not limitation. The scope of protection of the following claims is limited only by the claims themselves and not by the above description.

We claim:
1. A data distribution system, comprising:
  a personal area network (PAN) data blackboard comprising a first data storage space storing first data, wherein the PAN blackboard resides within a PAN, and wherein PAN nodes of the PAN utilize the PAN data blackboard for point-to-point communication within the PAN;
  a PAN node configured to monitor a first patient and write patient medical data concerning the first patient to the first data storage space, wherein the PAN node is coupled to the PAN data blackboard by way of the PAN and is configured in accordance with a publish-subscribe messaging model;
  a local area network (LAN) node that is configured in accordance with the publish-subscribe messaging model and subscribed to a data channel for receiving the patient medical data concerning the first patient; and
  a LAN data blackboard coupled to the PAN data blackboard by way of a LAN, wherein the LAN data blackboard comprises a second data storage space and a LAN data management node, wherein the second data storage space stores a subset of the first data that is selected by the LAN data management node, wherein the LAN data management node is configured: to determine that the LAN node is entitled to access the patient medical data concerning the first patient and, based on the LAN node being subscribed to the data channel and entitled to access the patient medical data concerning the first patient, to selectively synchronize data with the PAN data blackboard such that the patient medical data concerning the first patient is stored in the second data storage space for retrieval by the LAN node,
  wherein the LAN node is coupled to the LAN data blackboard by way of the LAN,
  wherein the LAN node is configured to read the patient medical data from the second data storage space and display the patient medical data, and
  wherein the PAN node is configured to send messages to the PAN data blackboard without regard to which subscribers, if any, there may be to the messages.

2. The data distribution system of claim 1, wherein the PAN node is configured to categorize the messages into classes.

3. The data distribution system of claim 1, wherein the PAN node comprises an application node residing in a medical device.

4. The data distribution system of claim 3, wherein the PAN node is configured to write the patient medical data to the PAN data blackboard in real-time.

5. The data distribution system of claim 4, wherein the LAN node is configured to display the patient medical data in real-time.

6. The data distribution system of claim 1, further comprising a wide area network (WAN) data blackboard coupled to the LAN data blackboard by way of a WAN.

7. A data distribution system, comprising:
a personal area network (PAN) data blackboard comprising a first data storage space storing first data, wherein the PAN blackboard resides within a PAN, and wherein PAN nodes of the PAN utilize the PAN data blackboard for point-to-point communication within the PAN;
a PAN node configured to monitor a first patient and write patient medical data concerning the first patient to the first data storage space, wherein the PAN node is coupled to the PAN data blackboard by way of the PAN and is configured in accordance with a publish-subscribe messaging model;
a wide area network (WAN) node that is configured in accordance with the publish-subscribe messaging model and subscribed to a data channel for receiving the patient medical data concerning the first patient; and
a WAN data blackboard coupled to the PAN data blackboard by way of a WAN, wherein the WAN data blackboard comprises a second data storage space and a WAN data management node, wherein the second data storage space stores a subset of the first data that is selected by the WAN data management node, wherein the WAN data management node is configured: to determine that the WAN node is entitled to access the patient medical data concerning the first patient and, based on the WAN node being subscribed to the data channel and entitled to access the patient medical data concerning the first patient, to selectively synchronize data with the PAN data blackboard such that the patient medical data concerning the first patient is stored in the second data storage space for retrieval by the WAN node,
wherein the WAN node is coupled to the WAN data blackboard by way of the WAN,
wherein the WAN node is configured to read the patient medical data from the second data storage space and display the patient medical data, and
wherein the PAN node is configured to send messages to the PAN data blackboard without regard to which subscribers, if any, there may be to the messages.

8. The data distribution system of claim 7, wherein the PAN node is configured to categorize the messages into classes.

9. The data distribution system of claim 7, wherein the PAN node comprises an application node residing in a medical device.

10. The data distribution system of claim 9, wherein the PAN node is configured to write the patient medical data to the PAN data blackboard in real-time.

11. The data distribution system of claim 10, wherein the WAN node is configured to display the patient medical data in real-time.

12. The data distribution system of claim 7, further comprising a local area network (LAN) data blackboard coupled to the WAN data blackboard by way of the WAN.

13. A data distribution system, comprising:
a personal area network (PAN) data blackboard comprising a first data storage space storing first data, wherein the PAN data blackboard resides within a PAN, and wherein PAN nodes of the PAN utilize the PAN data blackboard for point-to-point communication within the PAN;
a PAN node configured to monitor a first patient and write patient medical data concerning the first patient to the first data storage space, wherein the PAN node is coupled to the PAN data blackboard by way of the PAN and is configured in accordance with a publish-subscribe messaging model;
a local area network (LAN) node, wherein the LAN node: resides on a LAN that is separate from the PAN, is configured in accordance with the publish-subscribe messaging model, and is subscribed to a data channel for receiving the patient medical data concerning the first patient; and
a LAN data blackboard coupled to the PAN data blackboard by way of a LAN, wherein the LAN data blackboard comprises a second data storage space and a LAN data management node, wherein the second data storage space stores a subset of the first data that is selected by the LAN data management node, wherein the LAN data management node is configured to determine that the LAN node is _entitled to access the patient medical data concerning the first patient and, based on the LAN node being subscribed to the data channel and entitled to access the patient medical data concerning the first patient, to selectively synchronize data with the PAN data blackboard such that the patient medical data is stored in the second data storage space for retrieval by the LAN node,
wherein the LAN node is coupled to the LAN data blackboard by way of the LAN, and
wherein the LAN node is configured to read the patient medical data from the second data storage space and display the patient medical data.

14. The data distribution system of claim 13, wherein the patient medical data comprises an electrocardiogram sensor reading.

15. The data distribution system of claim 13, wherein the patient medical data comprises an audio stream or a video stream.

16. The data distribution system of claim 13, wherein the PAN node is configured to write the patient medical data to the PAN data blackboard in real-time.

17. The data distribution system of claim 16, wherein the LAN node is configured to display the patient medical data in real-time.

18. The data distribution system of claim 13, further comprising a wide area network (WAN) data blackboard coupled to the LAN data blackboard by way of a WAN.

* * * * *